(12) United States Patent
Kim

(10) Patent No.: US 10,478,275 B2
(45) Date of Patent: Nov. 19, 2019

(54) MEDICAL DIAGNOSTIC APPARATUS HAVING HEIGHT-ADJUSTABLE TABLE FOR ANIMALS

(71) Applicant: Ju-Hyung Kim, Seoul (KR)

(72) Inventor: Ju-Hyung Kim, Seoul (KR)

( * ) Notice: Subject to any disclaimer, the term of this patent is extended or adjusted under 35 U.S.C. 154(b) by 218 days.

(21) Appl. No.: 15/636,724

(22) Filed: Jun. 29, 2017

(65) Prior Publication Data

US 2018/0140408 A1 May 24, 2018

(30) Foreign Application Priority Data

Nov. 24, 2016 (KR) .................. 10-2016-0157186

(51) Int. Cl.
| | |
|---|---|
| *A61D 3/00* | (2006.01) |
| *A61G 13/06* | (2006.01) |
| *A61B 90/50* | (2016.01) |
| *A61B 6/04* | (2006.01) |
| *A61B 6/00* | (2006.01) |

(52) U.S. Cl.
CPC .............. *A61D 3/00* (2013.01); *A61B 6/0407* (2013.01); *A61B 6/508* (2013.01); *A61B 90/50* (2016.02); *A61G 13/06* (2013.01); *A61G 2210/50* (2013.01)

(58) Field of Classification Search
CPC ........... A61B 6/04; A61B 6/0407; A61B 6/56; A61B 3/00
See application file for complete search history.

(56) References Cited

U.S. PATENT DOCUMENTS

| | | | | |
|---|---|---|---|---|
| 2014/0133627 | A1* | 5/2014 | Sakuragi ............. | A61B 6/4429 378/62 |
| 2015/0124939 | A1* | 5/2015 | Ahn ..................... | A61B 6/4452 378/167 |
| 2015/0282780 | A1* | 10/2015 | Hamano ............... | A61B 6/484 378/36 |
| 2016/0081642 | A1* | 3/2016 | Okusu ................. | G06F 3/04845 378/62 |
| 2016/0081650 | A1* | 3/2016 | Okusu ................... | A61B 6/56 378/62 |

FOREIGN PATENT DOCUMENTS

| | | |
|---|---|---|
| KR | 10-2010-0005930 A | 1/2010 |
| KR | 10-0968217 B1 | 7/2010 |
| KR | 10-2012-0090290 A | 8/2012 |
| WO | WO-2016026817 A1 * 2/2016 ........... A61B 6/0407 |

* cited by examiner

*Primary Examiner* — Monica L Williams
*Assistant Examiner* — Aaron M Rodziwicz
(74) *Attorney, Agent, or Firm* — NSIP Law

(57) ABSTRACT

A medical diagnostic apparatus having a height-adjustable table for animals according to an embodiment of the present invention includes: a table where an animal is placed; a support stand supporting the table such that the table vertically moves and adjusting height of the table to move the table close to a floor; an X-ray detector disposed under the table and coupled to the support stand to move with the table; and an imaging stand spaced from the table, connected to the support stand, and having an X-ray tube for radiating X-rays to the X-ray detector.

4 Claims, 13 Drawing Sheets

MEDICAL DIAGNOSTIC APPARATUS HAVING HEIGHT-ADJUSTABLE TABLE FOR ANIMALS

CROSS REFERENCE TO RELATED APPLICATION

The present application claims priority to Korean Patent Application No. 10-2016-0157186, filed Nov. 24, 2016, the entire contents of which is incorporated herein for all purposes by this reference.

BACKGROUND OF THE INVENTION

Field of the Invention

The present invention relates to a medical diagnostic apparatus heaving a height-adjustable table for animals. More particularly, it relates to a medical diagnostic apparatus having a height-adjustable table for animals, the apparatus being able to take images with maximum SID 1800 mm of the distance between an X-ray detection unit and an X-ray tube by adjusting the heights of a table and a support stand.

Description of the Related Art

In general, medical X-ray diagnostic apparatuses, which are used to diagnose disease inside a body using images taken by X-rays, are apparatuses that analyze whether there is a broken bone inside a body at injured parts such as the chest, the head, the digestive system, and the backbone.

Medical diagnostic apparatuses, which are generally used at hospitals, refer to apparatuses that detect X-rays that pass through the body of a person or animal after being radiated from X-rays generated by an X-ray tube. According to medical X-ray diagnostic apparatuses, depending on the part to be X-rayed, both human patients and animals have to stand or lie on a table to be X-rayed.

As shown in FIG. 1A, a medical diagnostic apparatus 1 includes an imaging stand 2, an X-ray tube 3, a table 4, and a diagnostic body 5. The X-ray tube 3 is connected to the imaging stand 2 through an arm 2a and the arm 2a vertically moves along the imaging stand 2. The height of the X-ray tube 3 from the floor is adjusted by the arm 2a.

The table 4 is disposed over the diagnostic body 5. According to this structure, the table 4 is spaced as high as the height of the diagnostic body 5 from the floor.

An X-ray detection unit 8 is disposed on the diagnostic body 5. The X-ray detection unit 8 is disposed under the table 4. The X-ray detection unit 8 is a part that takes images of an object using X-rays from an X-ray tube 3. The X-ray detection unit 8 is also generally called an 'X-ray detector (DR)'.

The diagnostic body 5 is coupled to rails 6. As shown in FIG. 1B, the diagnostic body 5 can move left and right on the rails 6.

As shown in FIG. 1B, when taking an X-ray image of a side of an animal 10 using the medical diagnostic apparatus 1, it is required to secure a space around the lower portion of the imaging stand 2 so that the X-ray tube 3 can be positioned close to the floor. The diagnostic body 5 is moved on the rails 6 to secure the space. Thereafter, when the animal 10 is positioned between the X-ray tube 3 and a side X-ray detection unit 7, images of the animal 10 are taken by the medical diagnostic apparatus 1.

As described above, according to the medical diagnostic apparatus 1 of the related art, it is required to adjust the position of the diagnostic body 5 for the space charged by the X-ray tube 3 in order to take X-ray images of a side of the animal 10, so there is a need for a large space for installing the medical diagnostic apparatus 1. Accordingly, it may be difficult to efficiently use small spaces in individual animal hospitals or it may be impossible to install the medical diagnostic apparatus 1 due to insufficient spaces.

Further, the height of the table 4 is fixed to the height of the diagnostic body 5, so it is required to put the animal 10 on the table 4 in order to take X-ray images of the animal 10. Accordingly, when the animal 10 to be scanned with X-rays is heavy, it is difficult to put the animal 10 on the table 4.

Further, since the height of the table 4 is fixed, the distance between the X-ray tube 3 and the X-ray detection unit 8 is also fixed. In general, when SID is 1800 mm (SID 1800), the resolution of X-ray images is high. In other words, when the SID is 1800 mm, that is, the distance between the X-ray tube 3 and the X-ray detection unit 8 is 1.8 m, the resolution of X-ray images is high.

FIG. 2A shows an X-ray image at SID 1800 mm and FIG. 2B shows an X-ray image at SID 1000 mm.

Comparing FIGS. 2A and 2B, it can be seen that the X-ray image at SID 1800 mm is clearer than the X-ray image at SID 1000 mm. According to the medical diagnostic apparatus 1 of the related art, since the height of the table 4 is limited to the height of the diagnostic body 5, it is difficult to increase the distance between the X-ray tube 3 and the X-ray detection unit 8 up to 1.8 m.

SUMMARY OF THE INVENTION

Therefore, the present invention has been made in an effort to solve the problems and an object of the present invention is to provide a medical diagnostic apparatus having a height-adjustable table for animals, the apparatus being capable of adjusting the distance between an X-ray detector and an X-ray tube by adjusting the height of a table.

Another object of the present invention is to provide a medical diagnostic apparatus having a height-stable table for animals, the apparatus being capable of increasing convenience for taking images by allowing an animal to step on a table without requiring the animal to be placed on the table by a person by adjusting the height of the table close to the floor when the animal is heavy.

A further object of the present invention is to provide a medical diagnostic apparatus having a height-adjustable table for animals, the apparatus being capable of decreasing an installation space as much as the distance that a diagnostic body moves in the related art to obtain an X-ray image of a side of an animal, by changing the structure moving a diagnostic body left and right into a structure moving an imaging stand left and right with a table positioned close to the floor.

In order to achieve the above objects, according to an embodiment of the present invention, there is provided a medical diagnostic apparatus having a height-adjustable table for animals, the apparatus includes: a table where an animal is placed; a support stand supporting the table such that the table vertically moves and adjusting height of the table to move the table close to a floor; an X-ray detector disposed under the table and coupled to the support stand to move with the table; and an imaging stand spaced from the table, connected to the support stand, and having an X-ray tube for radiating X-rays to the X-ray detector.

The support stand may include: a support stand body having a stand guide rail on a side; a lifting member coupled to the stand guide rail to vertically move; a table actuator disposed in the support stand body, connected to the lifting member, and vertically moving the lifting member; and a table support coupling the lifting member and the table to each other.

The apparatus may further include an imaging stand support coupled to the support stand and supporting the imaging stand such that the imaging stand moves left and right.

The imaging stand support may include: a support frame coupled to the support stand and having a first lateral guide rail disposed in a width direction of the table; a lateral moving block supporting the imaging stand, having a plurality of rollers disposed on the first lateral guide rail, and disposed on the support frame to move left and right in a width direction of the support frame; a second lateral guide rail spaced from the first lateral guide rail and disposed on an inner side of the support frame; and a guide block coupled to the lateral moving block and having second rollers moving on the second lateral guide block, in which the distance between a side X-ray detector and the X-ray tube may be adjusted by moving the imaging stand left and right in order to take X-ray images of a side of an animal.

The imaging stand support may further include stoppers disposed at both sides of the support frame and restricting movement of the lateral moving block.

The imaging stand may include: an imaging stand body coupled to the lateral moving block and having an imaging stand guide rail on a side; an arm coupled to the imaging stand guide rail to vertically move on the imaging stand body and coupled to the X-ray tube; and an arm actuator disposed in the imaging stand body, connected to the arm, and vertically moving the arm.

According to the present invention, it is possible to increase convenience for taking images by allowing an animal to step on a table without requiring the animal to be placed on the table by a person by adjusting the height of the table close to the floor when the animal is heavy.

Further, it is possible to adjust the distance between the X-ray detector and the X-ray tube up to SID 1800 mm to take X-ray images by adjusting the height of the table and the support stand. Accordingly, it is possible to allow a veterinarian to precisely diagnose animals by using X-ray images at SID 1800 mm.

Further, since the imaging stand is moved left and right in the width direction of the table by the imaging stand support, it is possible to reduce the installation space as much as the distance that the diagnostic body moves in the related art to obtain X-ray images of a side of an animal. That is, according to medical diagnostic apparatuses in the related art, it was required to push a table to a side in order to secure a space for positioning an X-ray tube close to the floor. However, according to the present invention, since the imaging stand is moved left and right in the width direction of the table with the table positioned close to the floor, so it is possible to take X-ray images of a side of an animal on the table even without moving the table to another place.

Therefore, the apparatus of the present invention can be installed in relatively small spaces in comparison to the medical diagnostic apparatuses of the related art. Further, since the imaging stand is moved left and right in the present invention, it is possible to increase the resolution of X-ray images of a side of an animal by adjusting the distance between the X-ray tube and the side X-ray detector.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

A medical diagnostic apparatus having a height-adjustable table for animals according to an embodiment of the present invention is described hereafter with reference to the accompanying drawings.

According to the present invention it is possible to adjust the distance between an X-ray detector and an X-ray tube in order to secure predetermined resolution of an X-ray image by adjusting the height of a table.

Figure 3:
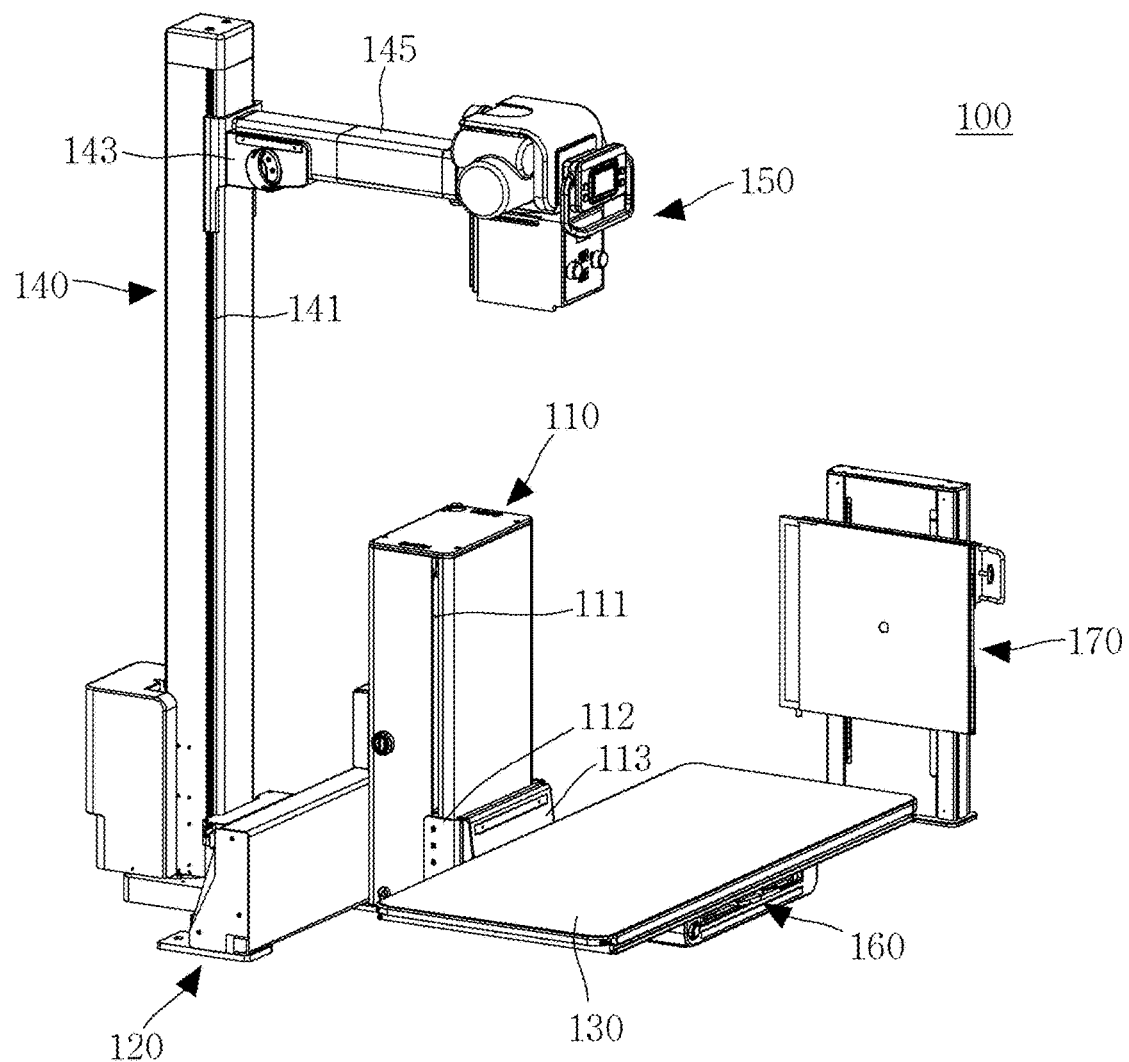
FIG. 3 is a front perspective view schematically showing a medical diagnostic apparatus having a height-adjustable table for animals according to the present invention and FIG. 4 is a rear perspective view schematically showing the medical diagnostic apparatus having a height-adjustable table for animals.
Figure 4:
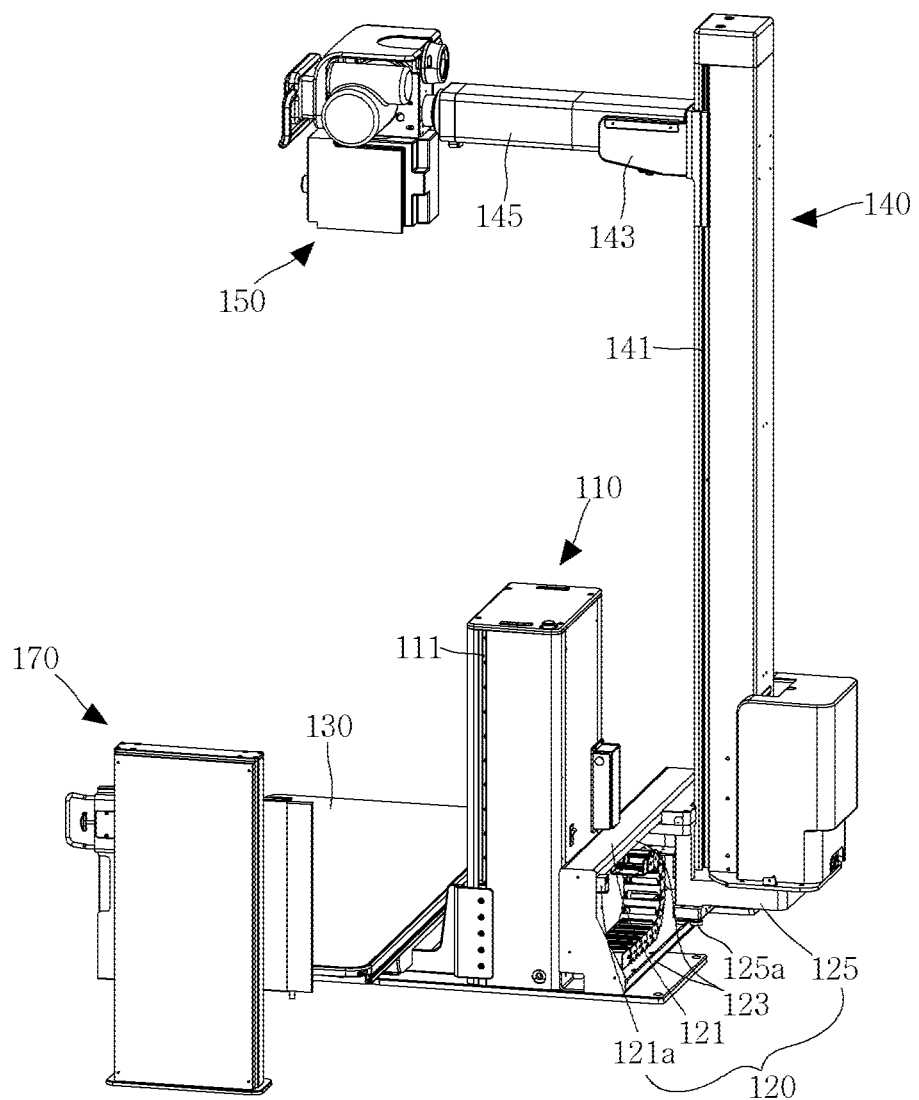
Figure 5:
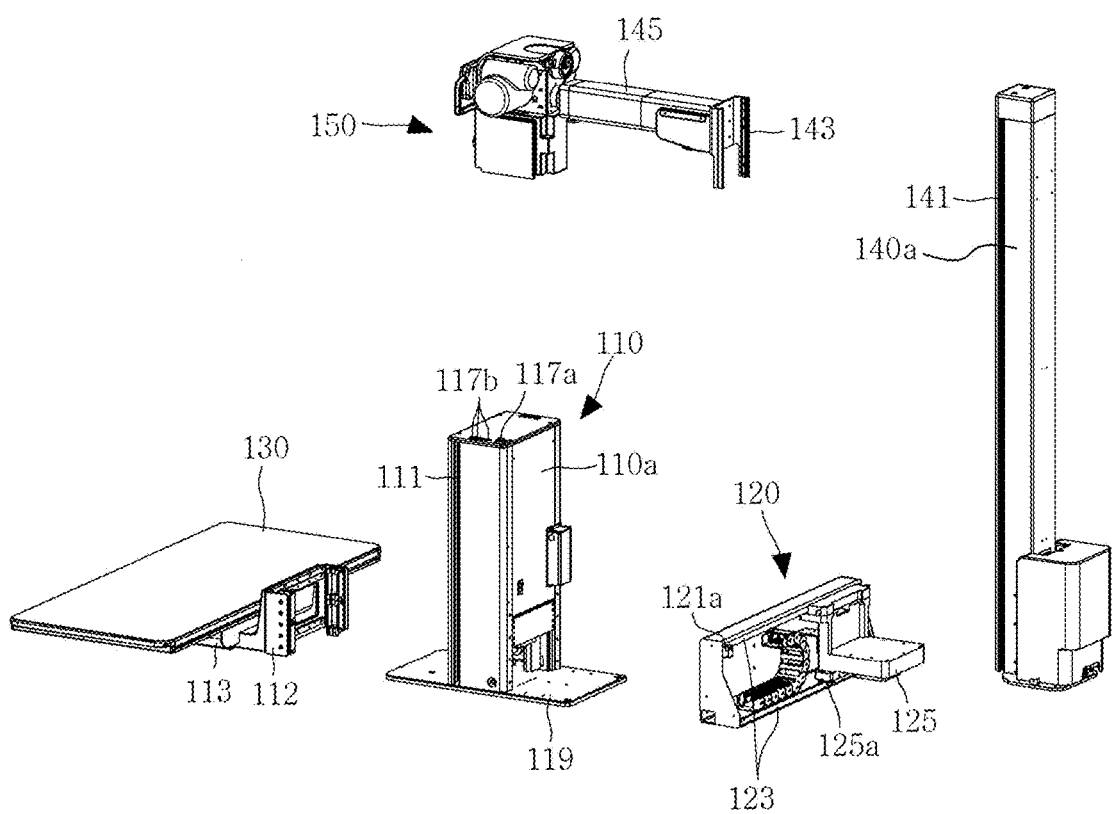
FIG. 5 is an exploded perspective view schematically showing the medical diagnostic apparatus having a height-adjustable table for animals according to an embodiment of the present invention.

As shown in FIGS. 3 to 5, a medical diagnostic apparatus 100 having a height-adjustable table for animals according to an embodiment of the present invention includes: a support stand 110, an imaging stand support 120, a table 130, an imaging stand 140, an X-ray tube 150, and an X-ray detector 160.

The support stand 110 supports the table 130 and allows for adjustment of the height of the table 130. The support stand 110 includes a support stand body 110a, a stand guide rail 111, a lifting member 112, a table actuator, a table support 113, and a bottom plate 119.

The bottom plate 119 is a flat plate that is placed on the floor. The support stand body 110a is disposed on the bottom plate 119. An operation button 117b and a power button 117a for operating the table actuator are disposed on the support stand body 110a.

The stand guide rail 111 is disposed on the support stand body 110a. The lifting member 112 is coupled to the stand guide rail 111. The operation button 117b and the power button 117a for operating the table actuator are disposed on the support stand body 110a.

The lifting member 112 is coupled to the table 130 through the table support 113. The lifting member 112 is coupled to the table actuator (not shown) in the support stand body 110a. In this embodiment, the configuration and structure of the table actuator (not shown) are not specifically limited as long as it can vertically move the lifting member 112.

The lifting member 112 vertically moves on the stand guide rail 111 when the table actuator (not shown) is operated. The table 130 moves in the same direction with the lifting member 112.

Figure 8A:
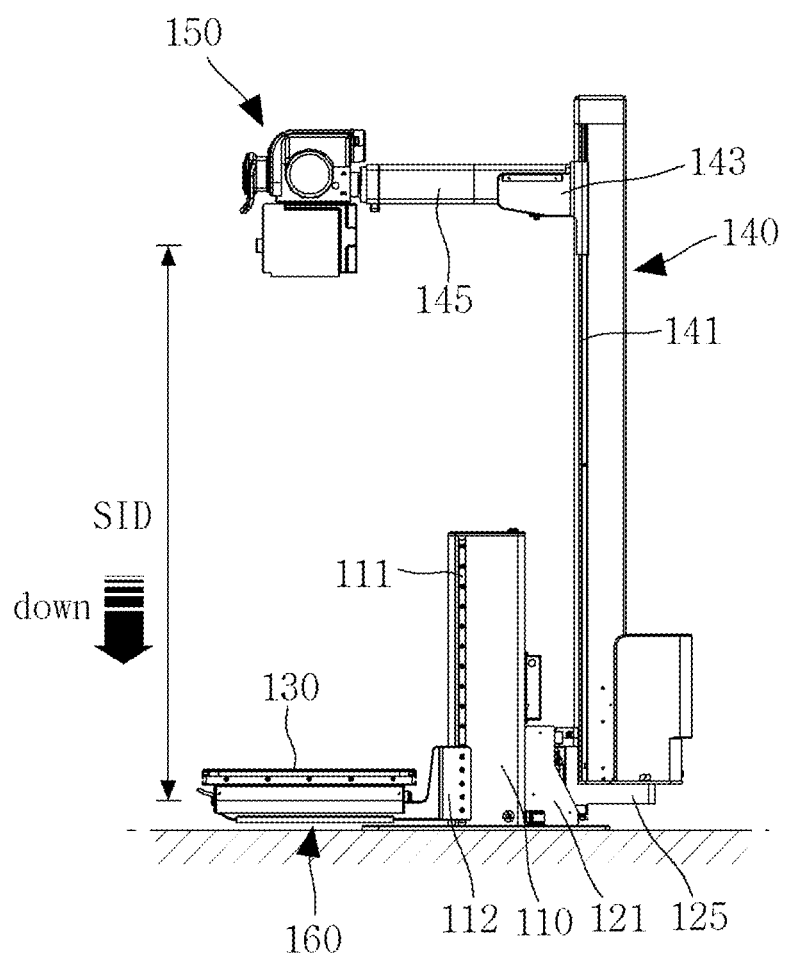
FIG. 8A is a side view schematically showing the medical diagnostic apparatus having a height-adjustable table for animals with the table positioned close to the floor and FIG. 8B is a side view of the medical diagnostic apparatus having a height-adjustable table for animals with the table lifted away from the floor.
Figure 8B:
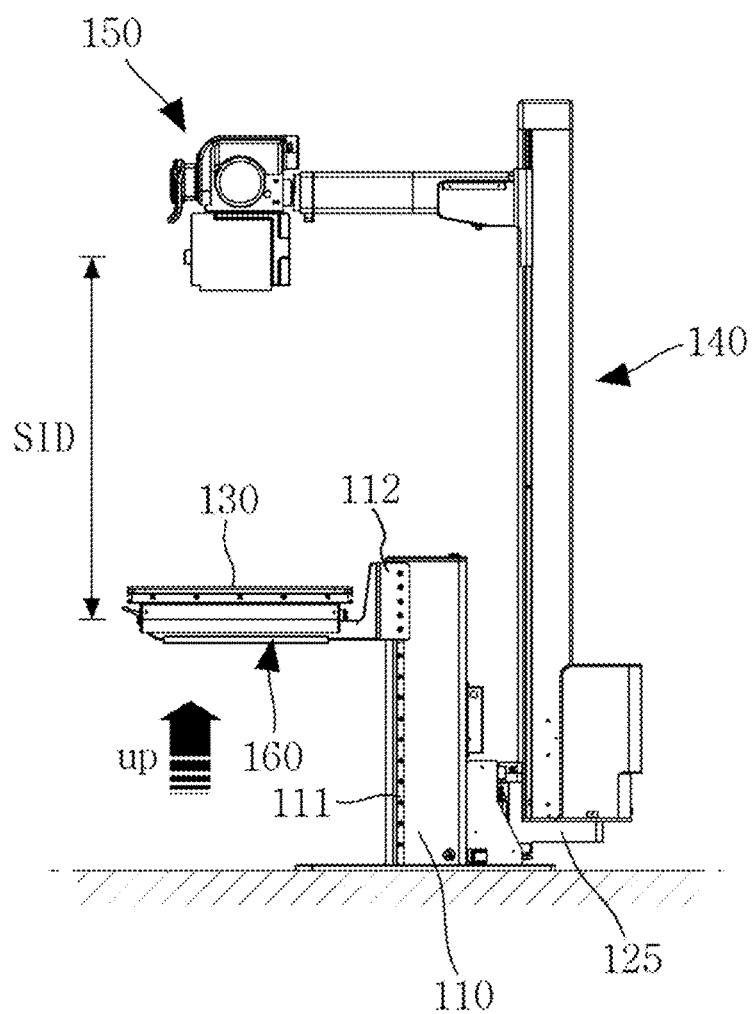

As shown in FIG. 8A, the table 130 can move down toward the floor on the stand guide rail 111 of the support stand 110. Alternatively, as shown in FIG. 8B, the table 130 can move up away from the floor on the stand guide rail 111 of the support stand 110. The table 130 is a part on which an animal 10 to be scanned is placed.

The X-ray detector 160 is disposed on the table support 113 under the table 130. Accordingly, the X-ray detector 160 is coupled to the support stand 110 and can vertically move along the support stand 110 together with the table 130. The X-ray detector 160 has an X-ray receiving surface for receiving X-rays from the X-ray tube 150. The X-ray receiving surface of the X-ray detector 160 is positioned in parallel with the floor.

Figure 7:
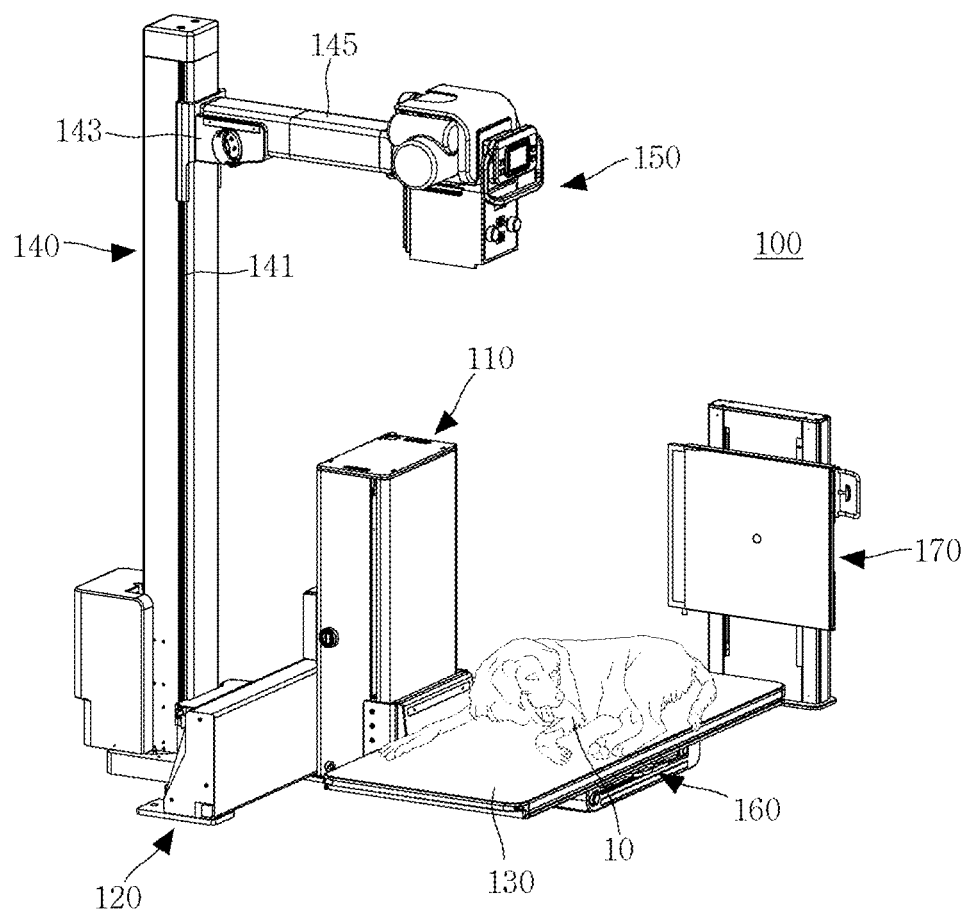
FIG. 7 is a view showing a case when an animal is put on a table.

As shown in FIG. 7, the support stand 110 having the structure described above can adjust the height of the table 130 close to the floor so that the animal 10 can step on the table 130. Accordingly, the medical diagnostic apparatus 100 having a height-adjustable table for animals of the present invention allows a user to easily take X-ray images of an animal.

Further, according to the present invention, it is possible to increase the distance (SID, Source to Image Distance) between the X-ray tube 150 and the X-ray detector 160 as large as possible through the lifting structure of the table 130. Therefore, the present invention allows a veterinarian to precisely diagnose animals through X-ray images at SID 1800. SID 1800 means that the distance between the X-ray tube 150 and the X-ray detector 160 is 1.8 m.

The imaging stand support 120 guides the imaging stand 140 moving left and right. When an X-ray image of a side of the animal 10 is taken, the imaging stand 120 guides the imaging stand 140 moving left and right to adjust the distance between a side X-ray detector 170 and the X-ray tube 150. The side X-ray detector 170 is disposed with an X-ray receiving surface perpendicular to the floor.

Figure 6:
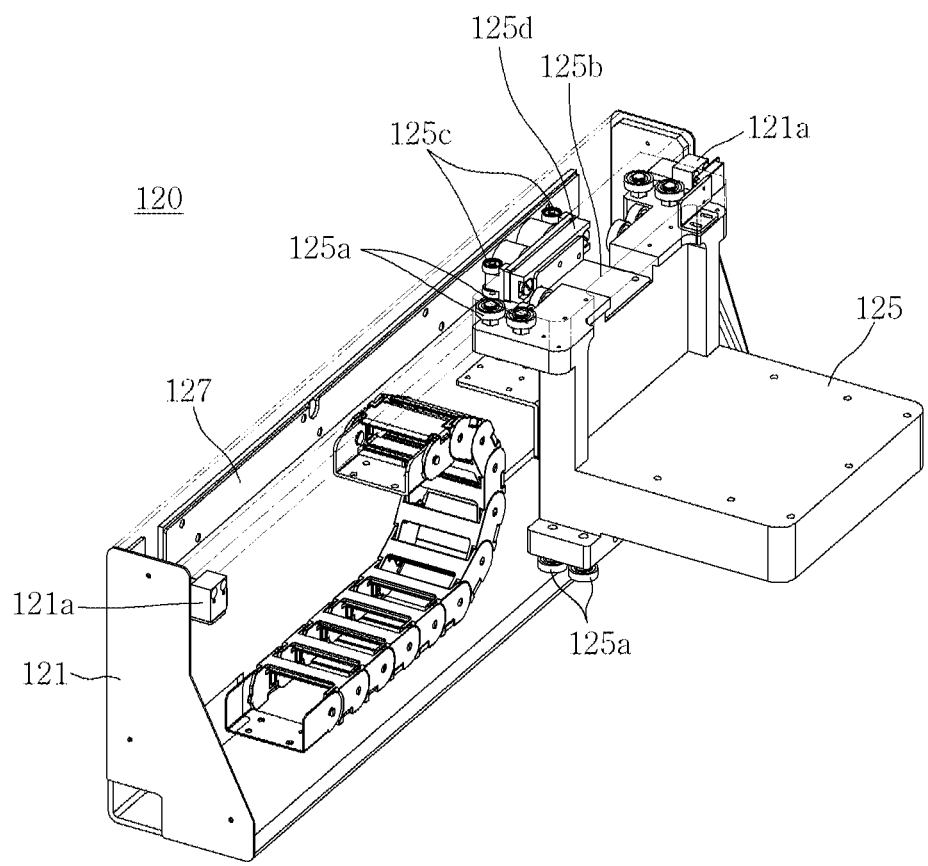
FIG. 6 is a view schematically showing a projective perspective view of an imaging stand support.

As shown in FIGS. 3 and 4, the imaging stand support 120 is coupled to the support stand 110. As shown in FIG. 6, the imaging stand support 120 includes a support frame 121, a lateral moving block 125, a first lateral guide rail 123, a second lateral guide rail 127, a guide block 125d and stoppers 121a.

A first side of the support frame 121 is in contact with a first side of the support stand body 110a. The support frame 121 is coupled to the support stand body 110a and the bottom plate 119. The first lateral guide rail 123 and the second lateral guide rail 127 are disposed on the support frame 121.

The first lateral guide rail 123 and the second lateral guide rail 127 guide the lateral moving block 125 moving left and right. The first lateral guide rail 123 and the second lateral guide rail 127 are arranged in the width direction of the table.

The first lateral guide rail 123 is disposed on a second side of the support frame 121. The second lateral guide rail 127 is disposed on the inner side of the support frame 121 and spaced from the first lateral guide rail 123.

The lateral moving block 125 is coupled to the imaging stand 140 to move the imaging stand 140 left and right. The lateral moving block 125 coupled to the support frame 121 can be moved left and right on the first lateral guide rail 123 by a plurality of rollers 125a.

The first rollers 125a are rotatably disposed at the upper and lower portions of the lateral moving block 125 and are coupled to the first lateral guide rail 123. The first rollers 125a can allow the lateral moving block 125 to smoothly move when the lateral moving block 125 moves left and right in the width direction of the support frame 121.

The lateral moving block 125 is coupled to the guide block 125d by a coupler 125b. Second rollers 125c are rotatably disposed on the guide block 125d. The second rollers 125c disposed on the guide block 125d can move on the second stand guide rail. When the lateral moving block 125 moves left and right in the width direction of the table 130, the guide block 125d guides the lateral moving block 125 while moving with the lateral moving block 125.

The movement distance of the lateral moving block 125 is limited by the stoppers 121a. The stoppers 121a are disposed at both sides of any one of the first lateral guide rails 123 on the support frame 121. The stoppers 121a prevent the lateral moving block 125 from separating from the first lateral guide rail 123 by restricting movement of the lateral moving block 125.

The imaging stand 140 supports the X-ray tube 150. The imaging stand 140 includes an imaging stand body 140a, an imaging stand guide rail 141, an arm 145, and an arm actuator (not shown).

The imaging stand body 140a is disposed on the lateral moving block 125. The imaging stand guide rail 141 is formed on the imaging stand body 140a. The imaging stand guide rail 141 guides the arm 145 vertically moving on the imaging stand body 140a.

The arm 145 is coupled to the imaging stand guide rail 141 by an arm connector 143. The arm connector 143 is coupled to the arm actuator (not shown). The arm actuator (not shown) is disposed in the imaging stand body 140a. The arm actuator provides a power to the arm connector 143. When the arm actuator is operated, the arm connector 143 vertically moves on the imaging stand guide rail 141.

The arm actuator is not specifically limited to the configuration and structure of this embodiment and may be modified within a range that is apparent to those skilled in the art as long as it can vertically move the arm 145. The configuration and the operation unit of the arm 145 are substantially the same as those of medical diagnostic apparatuses in the related art, so the structure of the arm 145 is not described in detail herein.

The X-ray tube 150 is coupled to the arm 145. The X-ray tube 150 is disposed at a position on the arm 145 where it can radiate X-rays to the X-ray detector 160. The height of the X-ray tube 150 from the floor is adjusted by moving the arm 145.

The X-ray tube 150 can be rotated at predetermined angles on the arm 145. Accordingly, as shown in FIG. 7, the X-ray tube 150 can be adjusted in angle to radiate X-rays to the X-ray detector 160. Alternatively, as shown in FIG. 10, the X-ray tube 150 can be adjusted in angle to radiate X-rays to the side X-ray detector 170.

Figure 10:
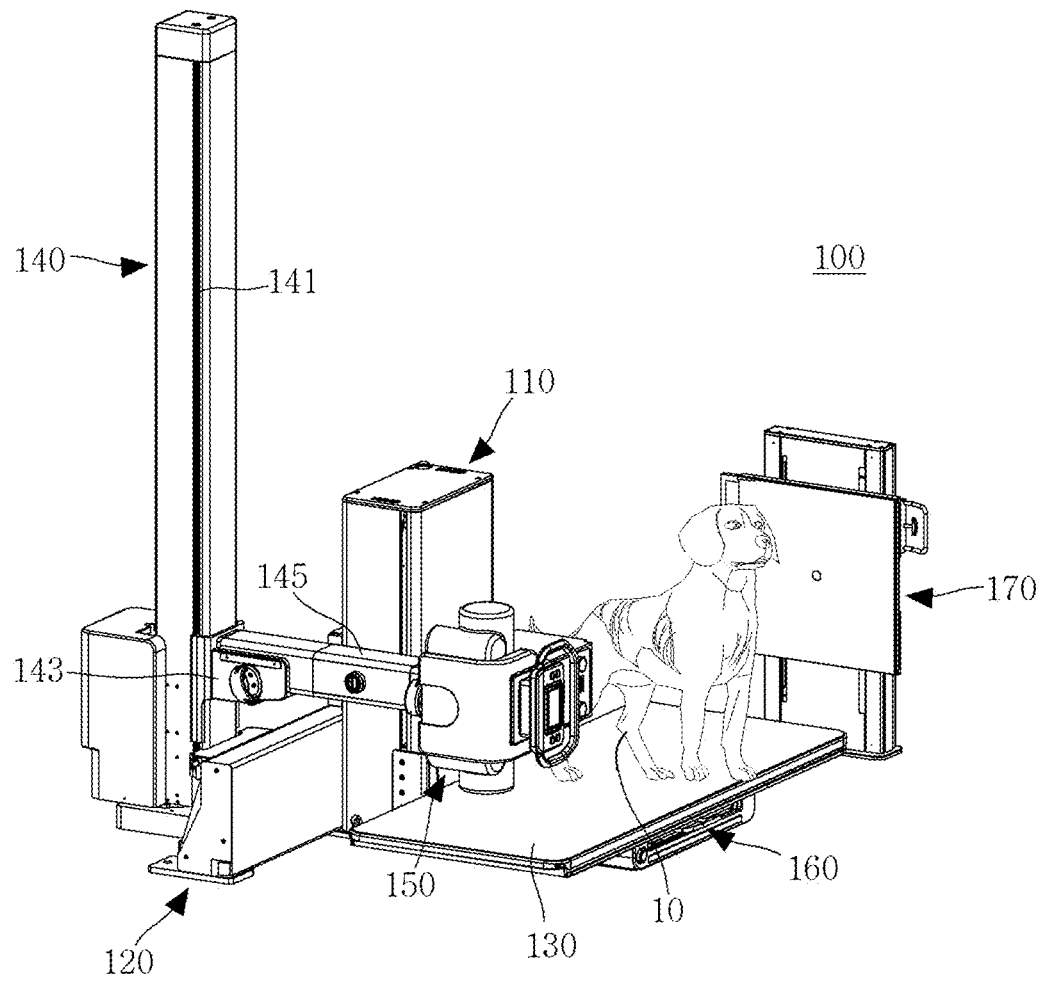
FIG. 10 is a view schematically showing the operation of the medical diagnostic apparatus having a height-adjustable table for animals when taking an X-ray image of a side of an animal.

As shown in FIG. 10, the side X-ray detector 170 is spaced from the table 130. The side X-ray detector 170 is provided to take X-ray images of a side of the animal 10.

In order to take X-ray images of a side of the animal 10, the medical diagnostic apparatus 100 having a height-adjustable table for animals operates as follows.

Figure 9:
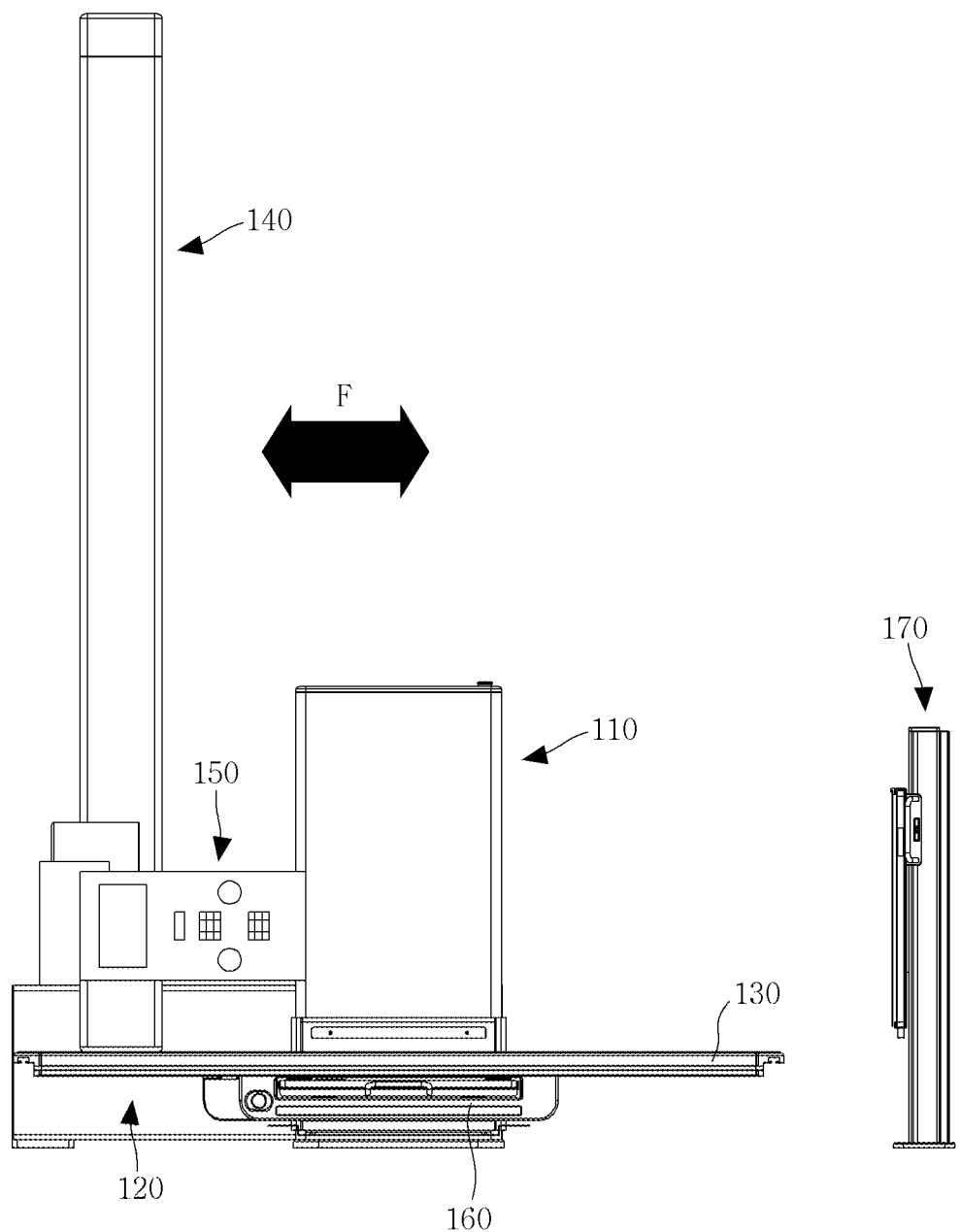
FIG. 9 is a front view schematically showing the medical diagnostic apparatus having a height-adjustable table for animals.

As shown in FIG. 9, the table 130 is moved close to the floor.

Thereafter, the imaging stand 140 can be moved in the width direction of the imaging stand support 120, that is, in the direction of an arrow close to or away from the side X-ray detector 170. This is for adjusting the distance between the side X-ray detector 170 and the X-ray tube 150.

Further, when the imaging stand is moved to a desired position, the arm 145 is moved down on the imaging stand guide rail 141 such that the X-ray tube 150 is positioned at a side of the animal 10.

When the positions of the table 130 and the X-ray tube 150 are determined through this operation, the animal 10 is allowed to step on the table 130. As shown in FIG. 10, the animal 10 is positioned between the X-ray tube 150 and the side X-ray detector 170.

Figure 1A:
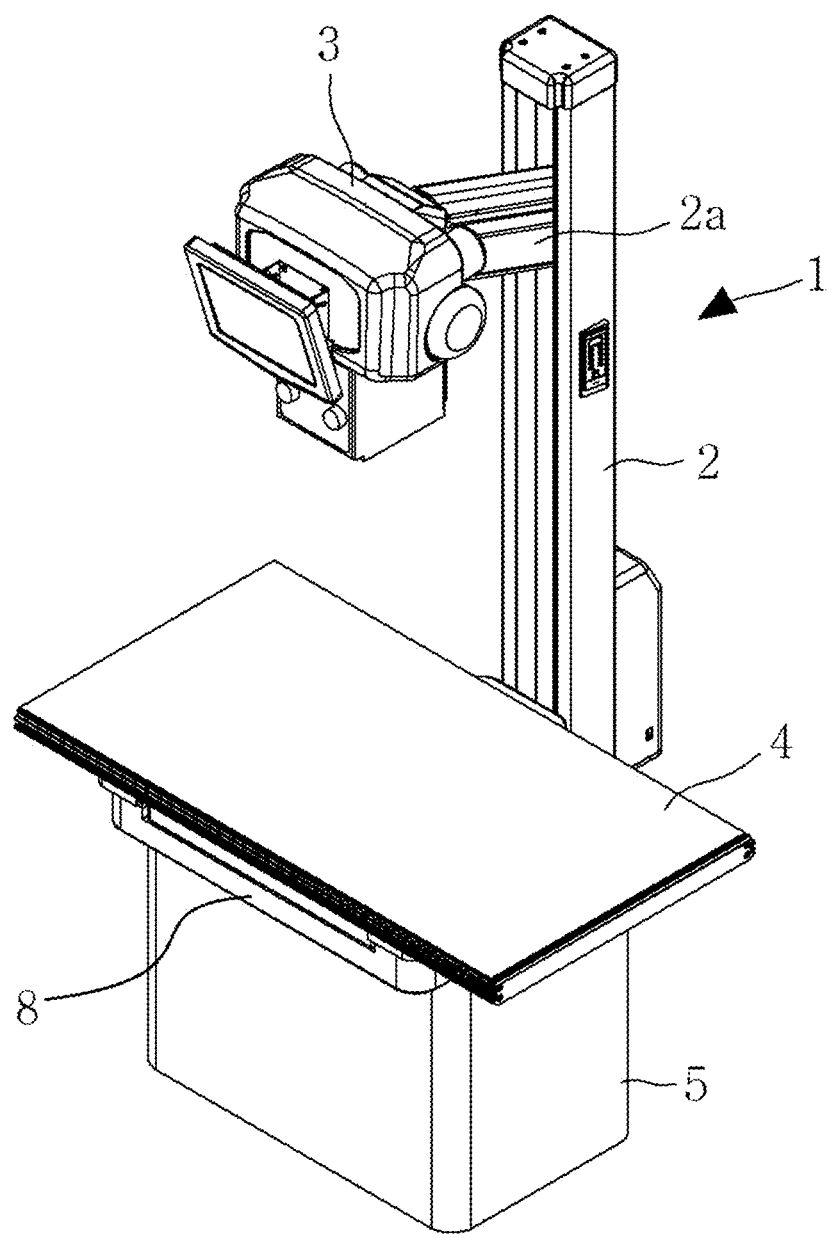
FIG. 1A is a perspective view schematically showing a medical diagnostic apparatus of the related art and FIG. 1B is a view schematically showing the operation of the medical diagnostic apparatus of the related art when taking an image of a side of an animal.
Figure 1B:
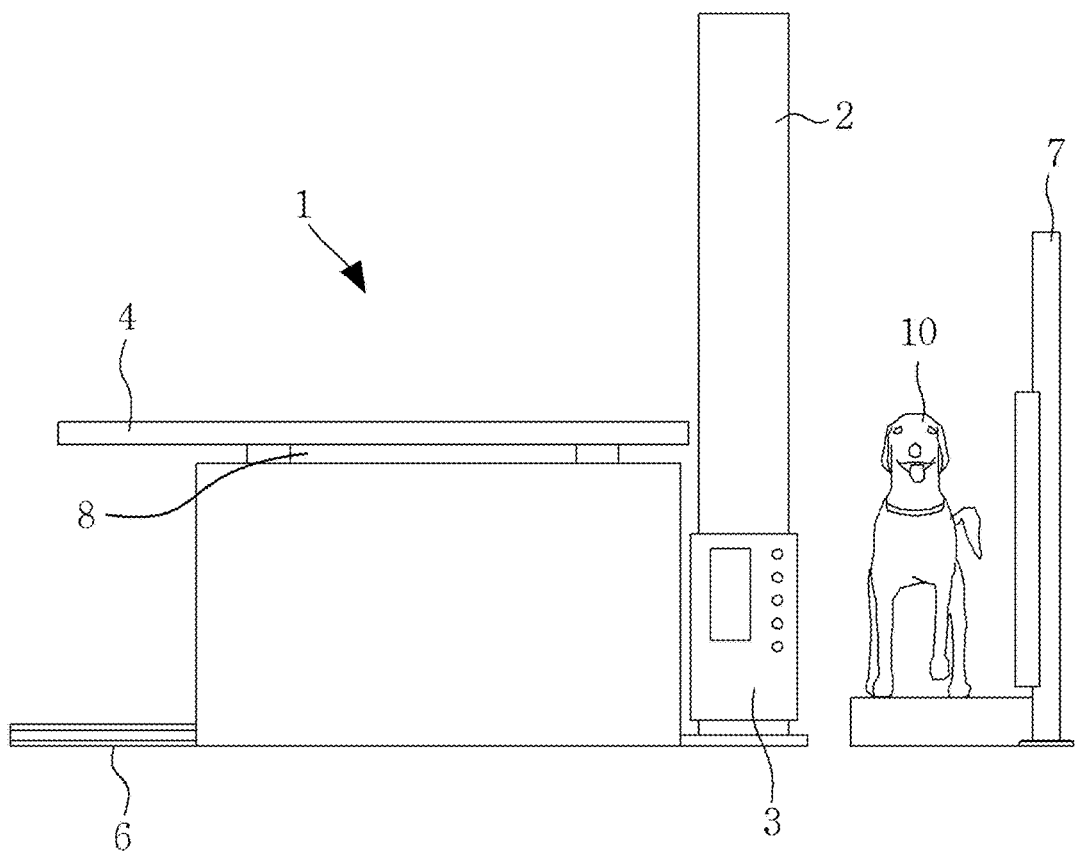
Figure 2A:
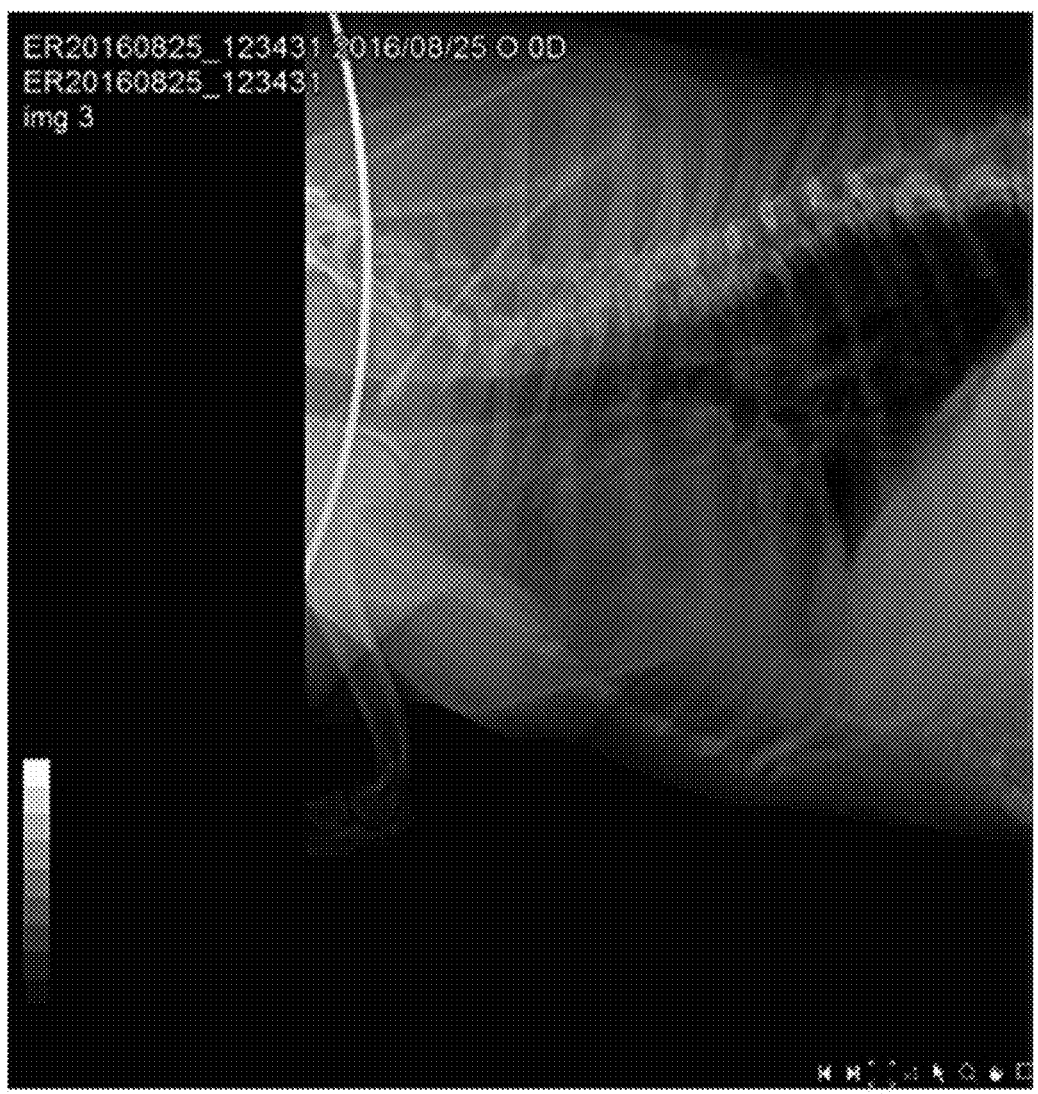
FIG. 2A is an X-ray image at SID 1800 and FIG. 2B is an X-ray image at SID 1000.
Figure 2B:
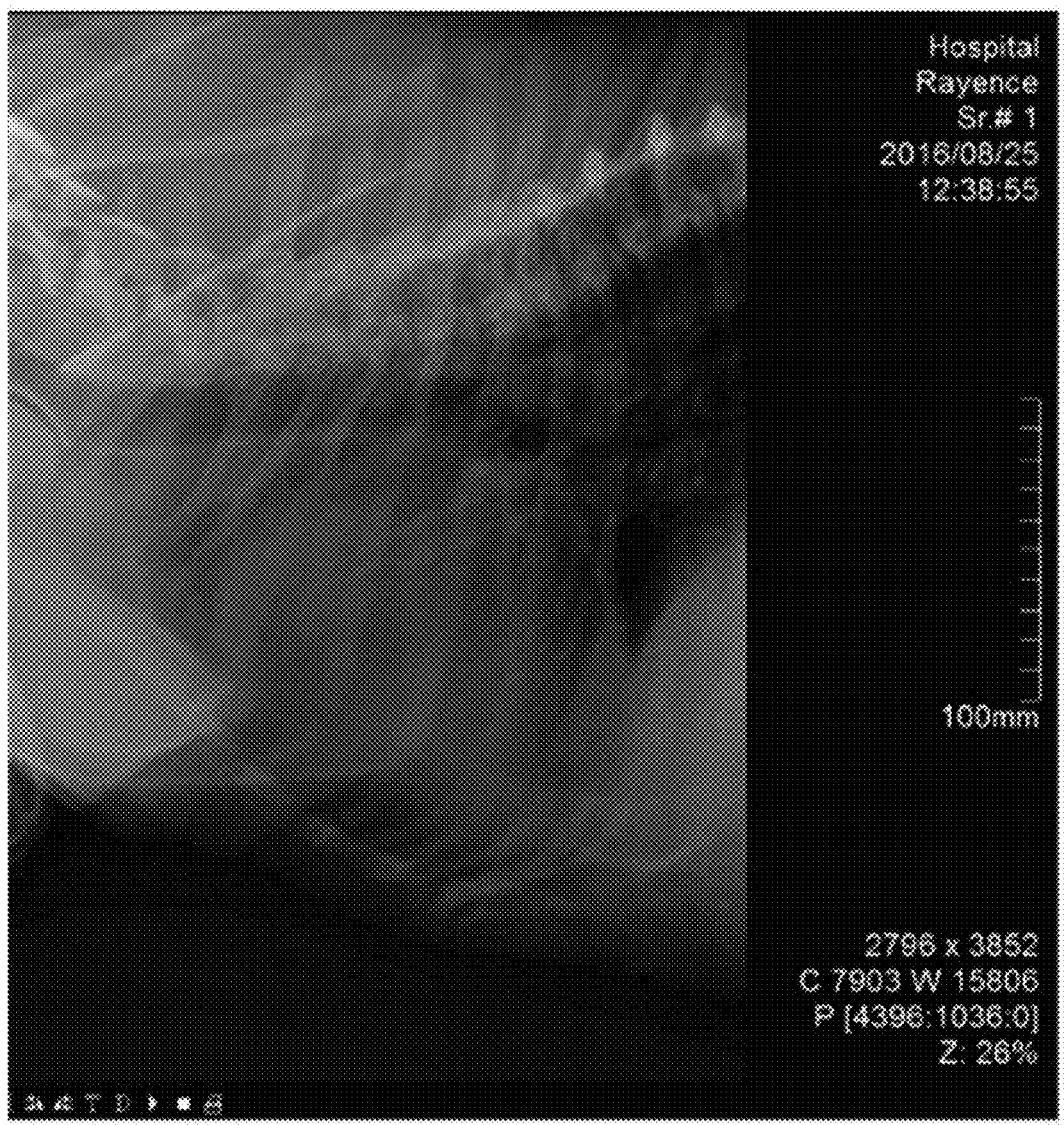

According to the present invention, the imaging stand 140 is moved left and right with the table 130 positioned close to the floor, so it is possible to reduce the installation space as much as the distance that the diagnostic body 5 (see FIG. 1B) moves in the related art to obtain X-ray images of a side of an animal.

Further, since the distance between the X-ray tube 150 and the side X-ray detector 170 is adjusted by moving the imaging stand 140 left and right on the imaging stand support 120, it is possible to increase the resolution of X-ray images of a side of the animal 10.

Although embodiments of the present invention were described above, it would be understood by those skilled in the art that the embodiments may be modified without departing from the spirit and scope of the present invention. The scope of the present invention should be determined by claims and equivalents of the claims.

What is claimed is:

1. A medical diagnostic apparatus having a height-adjustable table for animals, the apparatus comprising:
    a table where an animal is placed;
    a support stand supporting the table such that the table vertically moves and adjusting height of the table to move the table close to a floor;
    an X-ray detector disposed under the table and coupled to the support stand to move with the table;
    an imaging stand spaced from the table, connected to the support stand, and having an X-ray tube for radiating X-rays to the X-ray detector; and
    an imaging stand support coupled to the support stand and supporting the imaging stand such that the imaging stand moves left and right,
    wherein the imaging stand support comprises:
        a support frame coupled to the support stand and having a first lateral guide rail disposed in a width direction of the table;
        a lateral moving block supporting the imaging stand, having a plurality of rollers disposed on the first lateral guide rail, and disposed on the support frame to move left and right in a width direction of the support frame;
        a second lateral guide rail spaced from the first lateral guide rail and disposed on an inner side of the support frame; and
        a guide block coupled to the lateral moving block and having second rollers moving on the second lateral guide block, and
    wherein a distance between a side X-ray detector and the X-ray tube is adjusted by moving the imaging stand left and right in order to take X-ray images of a side of an animal.

2. The apparatus of claim 1, wherein the support stand includes:
    a support stand body having a stand guide rail on a side;
    a lifting member coupled to the stand guide rail to vertically move;
    a table actuator disposed in the support stand body, connected to the lifting member, and vertically moving the lifting member; and
    a table support coupling the lifting member and the table to each other.

3. The apparatus of claim 1, wherein the imaging stand support further includes stoppers disposed at both sides of the support frame and restricting movement of the lateral moving block.

4. The apparatus of claim 1, wherein the imaging stand includes:
    an imaging stand body coupled to the lateral moving block and having an imaging stand guide rail on a side;
    an arm coupled to the imaging stand guide rail to vertically move on the imaging stand body and coupled to the X-ray tube; and
    an arm actuator disposed in the imaging stand body, connected to the arm, and vertically moving the arm.

* * * * *